United States Patent
Samour et al.

[11] Patent Number: 5,976,566
[45] Date of Patent: Nov. 2, 1999

[54] NON-STEROIDAL ANTIINFLAMMTORY DRUG FORMULATIONS FOR TOPICAL APPLICATION TO THE SKIN

[75] Inventors: Carlos M. Samour, Bedford; Scott F. Krauser, Tyngsboro, both of Mass.; Robert J. Gyurik, Exeter, N.H.

[73] Assignee: MacroChem Corporation, Lexington, Mass.

[21] Appl. No.: 08/921,057

[22] Filed: Aug. 29, 1997

[51] Int. Cl.⁶ .......................... A61K 47/10; A61K 47/22; A61K 9/10

[52] U.S. Cl. .......................... 424/449; 424/484; 514/944; 514/946

[58] Field of Search .......................... 424/401, 484, 424/485, 487, 488; 514/944, 946

[56] References Cited

U.S. PATENT DOCUMENTS

| | | |
|---|---|---|
| 4,185,100 | 1/1980 | Rovee et al. . |
| 4,393,076 | 7/1983 | Noda et al. . |
| 4,533,546 | 8/1985 | Kishi et al. . |
| 4,861,764 | 8/1989 | Samoua et al. . |
| 5,093,133 | 3/1992 | Wisniewski et al. . |
| 5,350,769 | 9/1994 | Kasai et al. . |
| 5,374,661 | 12/1994 | Betlach, II. . |
| 5,422,102 | 6/1995 | Ikeda et al. . |
| 5,527,832 | 6/1996 | Chi et al. . |

OTHER PUBLICATIONS

Press Release, Lexington, MA, September 19, 1995 –MacroChem Corp.
Press Release, Lexington, MA, July 16, 1996 –MacroChem Corp.
L.C. Fuhrman, et al., Studies of In Vitro (Trans)Dermal Absorption . . . , Prediction of Percutaneous Penetration, vol. 4B, pp. 117–126, 1996.
Marty, et al., Effect of Dioxolanes On Indomethacin In Vitro . . . , Proceed. Intern. Symp. Control. rel. Bioact. Mater., 16, 179, 1989.

*Primary Examiner*—Edward J. Webman
*Attorney, Agent, or Firm*—Sherman and Shalloway

[57] ABSTRACT

Topical alcoholic or aqueous alcoholic gels containing ibuprofen or other NSAIDs, such as, naproxen, in substantially neutral salt form, have enhanced penetration through skin and may provide rapid pain/inflammation relief by including in the formulation 2-n-nonyl-1,3-dioxolane or other hydrocarbyl derivative of 1,3-dioxolane or 1,3-dioxane or acetal, as skin penetration enhancing compound. The amount of propylene glycol may be varied to adjust the initial flux of the NSAID through the skin, especially for ibuprofen, naproxen, and ketorolac.

13 Claims, 7 Drawing Sheets

- ■ — 2.5% Ibuprofen gel (E:PG:W:70:20:10)-10% SEPA®
- ● — 5% Ibuprofen gel (E:PG:W:70:20:10)-10% SEPA®
- ▲ — 10% Ibuprofen gel (E:PG:W:70:20:10)-10% SEPA®
- ◇ — 2.5% Ibuprofen gel (E:W:70:30)-10% SEPA®
- ◆ — 5% Ibuprofen gel (E:W:70:30)-10% SEPA®
- ○ — 10% Ibuprofen gel (E:W:70:30)-10% SEPA®

5,976,566

NON-STEROIDAL ANTIINFLAMMTORY DRUG FORMULATIONS FOR TOPICAL APPLICATION TO THE SKIN

FIELD OF INVENTION

This invention relates to topical compositions for transdermal administration of a non-steroidal antiinflammatory drug (NSAID) through the skin of a patient and to the method for transdermally administering the non-steroidal antiinflammatory drug using the topical composition.

DISCUSSION OF THE PRIOR ART

All drugs must be administered in such a manner that they reach the intended site in the body in an optimal concentration (amount of drug per unit volume of blood) to achieve the desired effect at the proper time, and for an appropriate length of time. Customarily, drugs are taken orally, injected, inhaled, or applied topically. These conventional routes of administration often fail to meet the stated objectives, however. For example, when drugs are absorbed into the blood stream by whatever route, peaks and valleys in the blood concentration of the drug occur and may cause undesirable effects (e.g., peak levels), or loss of activities (e.g., valleys). To meet these problems, a variety of approaches have been investigated. These include, for example, special drug coatings, combining the drug with other materials, suspensions or emulsions, and compressed tablets. Although these formulations attempt to control the release of drugs from their carriers, the desired effects are often not reproducible, may be subject to patient-to-patient variations, and may not be suitable for prolonged periods of delivery, such as days or even months.

Recent research has produced systems in which a drug is implanted in the body, released from skin sites, introduced in to the body by minipumps, and/or released in minute quantities through the skin. These innovative drug-delivery systems are improving drug effectiveness and also are opening opportunities for new pharmaceuticals.

The administration of drugs and other biological materials to the bloodstream via a transdermal route of administration has received much attention in recent years. The skin of an average adult covers more than two square meters of surface area and receives about one-third of all blood circulating through the body. It is elastic, rugged, and generally self-generating. The skin consists of three layers: the stratum corneum (S.C.), the epidermis, and the dermis. The stratum corneum represents the rate-limiting step in diffusion of chemical through the skin. The S.C. is composed of dead, keratinized, metabolically inactive cells which are closely packed together, and consists of an amorphous matrix of mainly lipoid and nonfibrous protein within which keratin filaments are distributed. The cells of the S.C. generally contain 20% water, while the cells below, in the stratum germinativum, contain 70% water. The S.C. does not become hydrated readily. Thus, transdermal permeation is primarily controlled by diffusion through the S.C.

There are several major reasons for the interest in devices for transdermal delivery of drugs:

- elimination of uncertainties of absorption from, and irritation to, the gastrointestinal tract which arise when drugs are administered orally.
- bypassing the portal circulation, thereby eliminating first-pass metabolism in the liver; this is extremely important for drugs with short half-lives, or with potential unwanted actions on the liver.
- delivery of medication directly into the systemic circulation at a constant rate (similar to intravenous infusion).
- infrequent dosing (daily, weekly or longer) for certain drugs.
- ease of use; foster patient compliance.

However, present transdermal delivery systems have major drawbacks. For example, they are restricted to low-molecular weight drugs and those with structures having the proper lipophilic/hydrophilic balance. High molecular weight drugs or drugs with too high or low hydrophilic balance often cannot be incorporated into current transdermal systems in concentrations high enough to overcome their impermeability through the stratum corneum.

Transdermal delivery is generally restricted to those medications requiring delivery rates less than 10 mg/day. In order to obtain higher blood levels, the rate of drug delivery must be increased. There have been many proposals to accomplish the higher rate of drug delivery via the use of absorption promoters and by the development of prodrugs that can be more readily absorbed. Examples of existing absorption enhancers include dimethyl sulfoxide (DMSO), ethylene glycol, hexanol, fatty acid and esters, and pyrrolidone derivatives, among others. One such enhancer compound which has received much attention is Azone (N-dodecyl azacycloheptan-2-one) developed by Nelson Research Labs., Irvine Calif.

One of the present applicants has previously developed a new class of compounds which are derivatives of 1,3-dioxanes and 1,3-dioxolanes for use as skin penetration enhancing compounds. These compounds, which have been made commercially available under the trademark SEPAL, are described in detail in U.S. Pat. No. 4,861,764. Work with the dioxolane enhancers has been described in several literature and patent publications. For example, Samour, et al., Proc. Int. Symp. Control. Rel. Bioact. Mater. 16: 183–184 (1989); Marty, et al., Proc. Int. Symp. Control. Rel. Bioact. Mater. 16:179–180 (1989); Marty, et al., Proc. Int. Symp. Control. Rel. Bioact. Mater. 17:415–416 (1990); Michniak, et al., Drug Delivery 2:117–122 (1995); Marty, et al., "Indomethacin and Ibuprofen Percutaneous Absorption In Vivo & In Vitro: Influence of 2-n-Nonyl-dioxolane On The Bioavailability" Abstract of Paper Presented at American Association of Pharmaceutical Scientists, Washington, D.C., Mar. 26–28, 1990.

In the article by Michniak, et al., the effect of the vehicle selected for the formulation was noted to play a very important role in the optimization of activity. In particular, it was noted that in certain cases propylene glycol was shown to possess a synergistic effect with Azone, depending on the model drug tested.

Propylene glycol was also used as a vehicle, usually together with ethanol and water, in the studies reported in the articles by Marty, et al. More specifically, in the above noted abstract, Marty et al report the effect of 2-n-nonyl-1,3-dioxolane (0.5%, w/w) with Ibuprofen or Indomethacin delivery in a vehicle system of propylene glycol (PG)/ethanol (EtOH) (50:50, v/v) or PG/EtOH/$H_2O$ (20/60/20, v/v), respectively. These studies were performed on the dorsal skin of hairless female rats or, in some cases, human skin. The formulations containing the enhancer were more effective than control and more effective than compositions containing Azone as the enhancer.

The use of an aqueous alcoholic gel for the percutaneous delivery of Ibuprofen is the subject of U.S. Pat. No. 5,093,133. The gel contains, by weight of the total formulation, about 1 to 15% S-ibuprofen, 0 to 20% propylene glycol; about 40 to 60% alcohol; about 2.0 to 5.0% gelling agent and pH modifier to obtain an acidic pH in the range of 3.5 to 6.0. The rate of delivery of Ibuprofen is stated to be pH dependent. Use of skin penetration enhancing compound is not disclosed.

In addition to the background literature referred to in the U.S. Pat. No. 5,093,133, the following patents relate to topical formulations for the transdermal delivery of NSAIDS: U.S. Pat. Nos. 4,185,100; 5,164,416, 5,374,661. The latter of these patents is particularly concerned with a neutral pH composition for transdermal delivery of diclofenac and uses a mixture of water, low molecular weight alcohol and a glycol. The addition of the glycol is stated to enhance the transdermal delivery of diclofenac. Data in this patent shows that dipropylene glycol and hexylene glycol provided higher skin flux through human skin than with propylene glycol. This patent further states that the effectiveness of topical diclofenac in treating inflammation and/or painful joints and muscles depends significantly on the particular skin penetrating vehicle with which it is used. These patentees use ether alcohols or fatty alcohol esters to enhance the transdermal permeation of diclofenac.

The present inventors have continued to study the effect of the 1,3-dioxane and 1,3-dioxolane derivatives and related acetals as skin penetration enhancer compounds for ibuprofen and other NSAIDs. Surprisingly, it has been found that when propylene glycol is used in the vehicle for the ibuprofen formulations, but not for other NSAIDS, such as diclofenac, ketoprofen, piroxicam, the initial flux rate of ibuprofen decreased as the amount of propylene glycol (PG) increased. Just the opposite effect was observed for the other tested NSAID compounds. In both cases, however, the total payload over a twenty-four hour period is substantially the same. That is, the area under the curve obtained by plotting flux rate over time is the same at 24 hours but the profile of the curves for ibuprofen is dramatically different than for the other tested NSAID compounds.

The present inventors also discovered that at the lower pH's most effective for enhancing the flux of ibuprofen, the 1,3-dioxolane and 1,3-dioxane penetration enhancing compounds become unstable. Applicants have been able to overcome this problem by incorporating the ibuprofen in the form of its substantially neutral (e.g., pH=about 6 to about 8, preferably about 6.5 to 7.5) salt by neutralizing the formulation using an appropriate base, such as sodium hydroxide. This observation of enhancement of the transdermal drug delivery at neutral pH was unexpected since it was originally thought that neutralization of the drug would make it less lipophilic and inhibit its diffusion through the stratum corneum.

It has further been discovered that the flux rates and/or total delivery of NSAIDs, such as, for example, diclofenac, are substantially improved using the 1,3-dioxolane, 1,3-dioxane or corresponding acetal compound skin penetration enhancing compounds.

Another surprising discovery by the present inventors is that for certain of the NSAID active ingredients, such as, naproxen, the permeation through the skin is further enhanced when glycol, e.g., propylene glycol, is omitted from the formulation.

SUMMARY OF INVENTION

The present invention has as a principal object to provide stable topical compositions effective for the transdermal application of ibuprofen or other NSAID compounds by the application of the composition to the skin.

The above and other objects of the invention, which will become more apparent from the following more detailed description and preferred embodiments is achieved, according to a first aspect of the invention, by an ibuprofen containing alcoholic or aqueous alcoholic composition which comprises, on a weight basis, of the total composition:

a therapeutically effective amount of ibuprofen in the form of its pharmacologically acceptable salt;

a skin penetration enhancing effective amount of a $C_7$ to $C_{14}$-hydrocarbyl substituted 1,3-dioxolane, 1,3-dioxane or acetal;

0 to about 18% of glycol having from 3 to 6 carbon atoms;

at least 40% of volatile alcohol selected from the group consisting of ethanol, propanol and mixture thereof;

0 to about 40% water; and, base to provide a pH in the range of from about 6 to about 8; and optionally, a gelling agent effective to thicken the composition to avoid or minimize run-off when applied to the skin.

In a preferred embodiment of this aspect of the invention the ingredients are included in the formulation in the following ranges:

from about 2 to 10% ibuprofen;

from about 2 to 15% of the enhancer wherein the hydrocarbyl group substituent has from about 7 to 10 carbon atoms;

from about 0 to 15% propylene glycol;

from about 55 to 70% ethanol, isopropanol or mixture thereof;

from about 4 to 35% water; and, base to provide a pH in the range of from about 6.5 to about 7.5; and 0 to about 2% of cellulosic thickener.

According to another aspect of the invention there are provided alcoholic or aqueous alcoholic topical compositions effective for the transdermal delivery of non-steroidal antiinflammatory drug which comprises, based on the weight of the total composition, a therapeutically effective amount of a non-steroidal antiinflammatory drug selected from the group consisting of heteroaryl acetic acids, arylpropionic acids (other than ibuprofen), anthranilic acids, enolic acids, alkanones, sulindac and etodolac;

0.5 to about 25% of $C_7$ to $C_{14}$-hydrocarbyl derivative of 1,3-dioxolane, 1,3-dioxane or acetal as skin penetration enhancer;

0 to about 40% of a glycol having from 3 to 6 carbon atoms;

at least about 40% of volatile alcohol selected from the group consisting of ethanol, propanol and mixtures thereof;

0 to about 40% water; and base to provide a pH of from about 6 to about 8; and 0 to about 5% gelling agent.

According to a preferred embodiment of this second aspect of the invention the composition comprises:

from about 0.1 to 10% diclofenac, ketorolac, naproxen, flurbiprofen, ketoprofen or piroxicam;

from about 2 to 15% of the skin penetration enhancer;

0 to about 30% propylene glycol;

from about 35 to 70% ethanol or isopropanol or mixture thereof;

0 to about 20% water;

base to provide a pH in the range of from about 6.5 to about 7.5; and up to about 3% gelling agent.

In still yet another aspect of the invention, the NSAID is naproxen and the glycol component is eliminated from the formulation. According to this third aspect of the invention, there are provided glycol-free topical compositions effective for the transdermal administration of naproxen, which comprise, on a weight basis of the total composition:

a pharmaceutically effective amount of pharmacologically acceptable salt of naproxen, from about 2 to 20% of 2-hydrocarbyl group substituted 1,3-dioxolane, 1,3-dioxane, or acetal skin penetration enhancer wherein the hydrocarbyl group has from 7 to 14 carbon atoms;

from about 50 to 85% ethanol and/or iso-propanol;

0 to about 40% water; and base in amount to provide a pH in the range of from about 6 to about 8; and up to about 5% gelling agent.

DETAILED DESCRIPTION AND PREFERRED EMBODIMENTS

Figure 1:
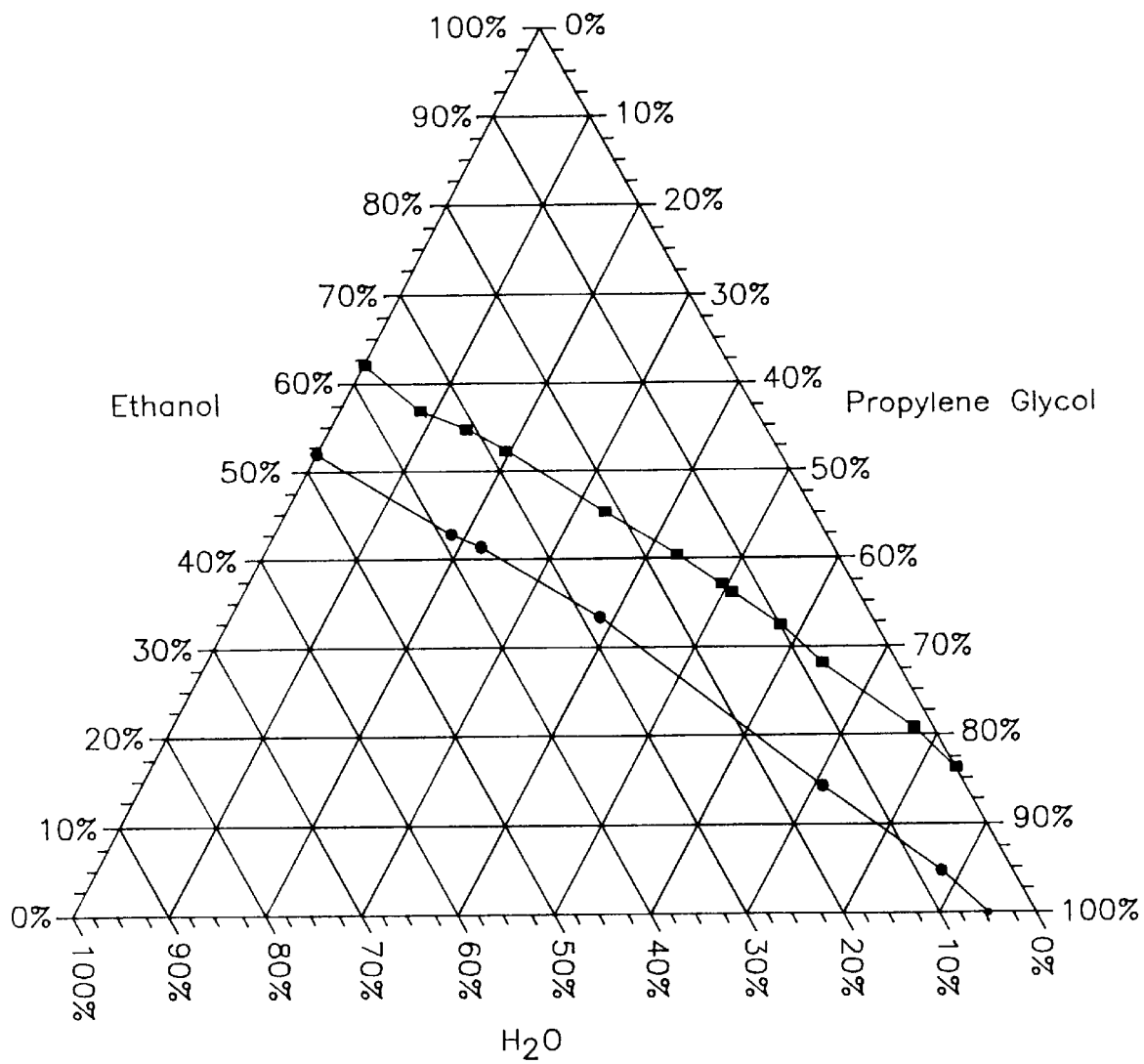
FIG. 1 is a ternary phase diagram showing the miscibility of 2-n-nonyl-1,3-dioxolane skin penetration enhancer at 10 wt. % (■) or 2 wt. % (●) in an ethanol-propylene glycol-water vehicle.

The compositions of the invention are intended for topical, non-invasive, application to the skin, particularly to the region where the non-steroidal anti-inflammatory active ingredient is intended to exert its pharmacological activity, usually to a region of inflammation, injury or pain to the muscles or joints, or other form of cutaneous disorders or disruptions characterized by skin inflammation and/or hyperproliferative activity in the epidermis.

Examples of the non-steroidal antiinflammatory drug (NSAID) which is advantageously administered by the topical formulations of this invention include heteroaryl acetic acids, such as, for example, tolmetin, diclofenac, ketorolac; arylpropionic acids, such as, for example, ibuprofen, naproxen, flurbiprofen, ketoprofen, fenoprofen, oxaprozin; anthranilic acids (fenamates), such as, for example, mefenamic acid, meclofenamic acid, fhilenamic acid; enolic acids, such as, for example, oxicams (e.g., piroxicam, tenoxicam), pyrazolidinediones (e.g., phenylbutazone, oxyphenthatrazone); alkanoes, such as, for example, nabumetone. Among these, especially preferred, based on the current level of knowledge in the pharmacological arts, are ibuprofen, diclofenac, ketorolac, naproxen, flurbiprofen, ketoprofen and piroxicam. More generally, however, any of the government approved NSAIDs, such as listed in, for example, the most current edition of The Merck Index, may be advantageously used.

According to the present invention the NSAID is administered in the form of its pharmacologically acceptable substantially neutral salt. The formulations are made substantially neutral by addition of a pH modifying agent (base) in an amount to provide a pH in the range of from 6.0 to 8.0, preferably from 6.5 to 7.5, especially preferably from 6.8 to 7.4, such as 7.0. Any of the well known and pharmacologically safe inorganic or organic basic compounds can be used for this purpose and examples include inorganic salt, such as the sodium or other alkali or alkaline earth metal salts such as hydroxides, e.g., sodium hydroxide or potassium hydroxide; ammonium salt; or organic salt, especially amine salt, such as, for example, diethylamine; diethanolamine, triethanolamine, diisopropanolamine, N-methylglucamine, ethanolamine, isopropylamine, tetrahydroxypropyl ethylene diamine methylamine, ethylamine, propylamine, and the like.

For any particular formulation the NSAID and other ingredients may be selected to achieve the desired drug delivery profile and the amount of penetration desired. The optimum pH may then be determined and will depend on, for example, the nature of the NSAID, the base, and degree of flux required.

The penetration of the active ingredient through the skin is enhanced to an acceptable level by including in the composition a skin penetration enhancing effective amount of an enhancer compound of the substituted 1,3-dioxacyclopentane and substituted 1,3-dioxacyclohexane types disclosed in U.S. Pat. No. 4,861,764, the disclosure of which is incorporated herein in its entirety by reference thereto, or the corresponding substituted acetal compound. Representative examples of the skin penetration enhancing compounds include:

2-substituted 1,3-dioxolanes of the formula (I):

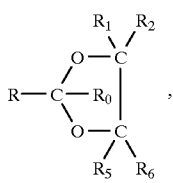
(I)

2-substituted 1,3-dioxanes of the formula (II):

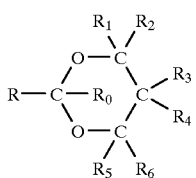
(II)

substituted-acetals of the formula (III):

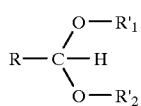
(III)

In the above formulas (I), (II) and (III) R preferably represents a $C_7$ to $C_{14}$ hydrocarbyl group, $R_0$, $R_1$, $R_2$, $R_3$, $R_4$, $R_5$, and $R_6$, each, independently, represent hydrogen or a $C_1$ to $C_4$ alkyl group.

$R'_1$ and $R'_2$, each, independently, represent $C_1$ to $C_4$ alkyl group.

The hydrocarbyl group for R may be a straight or branched chain alkyl, alkenyl or alkynyl group, especially alkyl or alkenyl. Preferably, R represents a $C_7$ to $C_{12}$ aliphatic group; especially $C_7$ to $C_{10}$ aliphatic group. Examples of suitable alkyl groups include, for example, n-hexyl, n-heptyl, n-octyl, n-nonyl, n-decyl, n-undecyl, n-dodecyl, 2-methyl-octyl, 4-ethyl-decyl, 8-methyl-decyl, and the like. The straight chain alkyl groups, such as n-heptyl, n-octyl, n-nonyl and n-decyl, are especially preferred. Examples of alkenyl groups include, for example, 2-hexenyl, 2-heptenyl, 2-octenyl, 2-nonenyl, 2',6'-dimethyl-2',6'-heptadienyl, 2',6'-dimethyl-2'heptaenyl, and the like. The R group may also be substituted by, for example, halo, hydroxy, carboxy, carboxamide and carboalkoxy.

The $C_1$ to $C_4$ alkyl group may be, for example, methyl, ethyl, n-propyl, isopropyl, n-butyl, tert-butyl, and the like. The preferred alkyl groups for $R_0$, and for $R_1$ to $R_6$ and for $R'_1$ and $R'_2$ are alkyl having 1 or 2 carbon atoms, most especially ethyl. $R_0$, and $R_1$ to $R_6$ may also, preferably, all be hydrogen.

Specific enhancer compounds include, for example, 2-n-pentyl-1,3-dioxolane, 2-n-heptyl-1,3-dioxolane, 2-n-nonyl-1,3-dioxolane, 2-n-undecyl-1,3-dioxolane, 2-n-nonyl-1,3-dioxane, 2-n-undecyl-1,3-dioxane, 2-n-heptylaldehyde-acetal, 2-n-octyl-aldehyde-acetal, 2-n-nonylaldehyde-acetal, 2-n-decylaldehyde-acetal, 3,7-dimethyl-2,6-octadienal (citral), citronal and the like. 2-n-nonyl-1,3-dioxolane is especially preferred and is commercially available from MacroChem Corporation of Lexington, Mass., under the trademark SEPA®.

The amount of the enhancer compound is selected to provide the desired delivery rate for the active compound but, taking into consideration such additional factors as, product stability, side effects, carrier system and the like. Generally, depending on the particular NSAID and other vehicles, amounts in the range of from about 0.5 to 25%, preferably from about 2 or 3 or 4 to 12 or 15 or 20 percent, especially from about 5 to 10 percent, of the composition, will provide optimal flux rate and 24 hour payload of the active ingredient. Usually, for cream formulations the amount of enhancer compound may be lower than for gel formulations, such as from about 2 to 10 percent of the formulation.

The compositions are generally formulated as gels, especially aqueous-alcoholic gels. However, other forms, such as, for example, lotions, creams, mousses, aerosols, ointments, lubricants, etc., may be used so long as when applied to the affected area of the skin the formulation will stay in place, i.e., without run-off, for sufficient time, to permit an individual to spread and retain the composition over and on the affected area.

The vehicle for any of the forms of the compositions of the invention will include glycol, e.g., propylene glycol, butylene glycol, hexylene glycol, etc. (except in the case of the third embodiment described above), lower alcohol, e.g., ethanol, isopropanol, and, usually, water. A thickening or gelling agent is also usually and preferably included to facilitate application of the formulation to the skin. In addition, of course, the skin penetration enhancing dioxolane, dioxane or acetal is included in the formulations in an amount effective to enhance the penetration of the active NSAID ingredient through the skin, including the stratum corneum.

Figure 2:
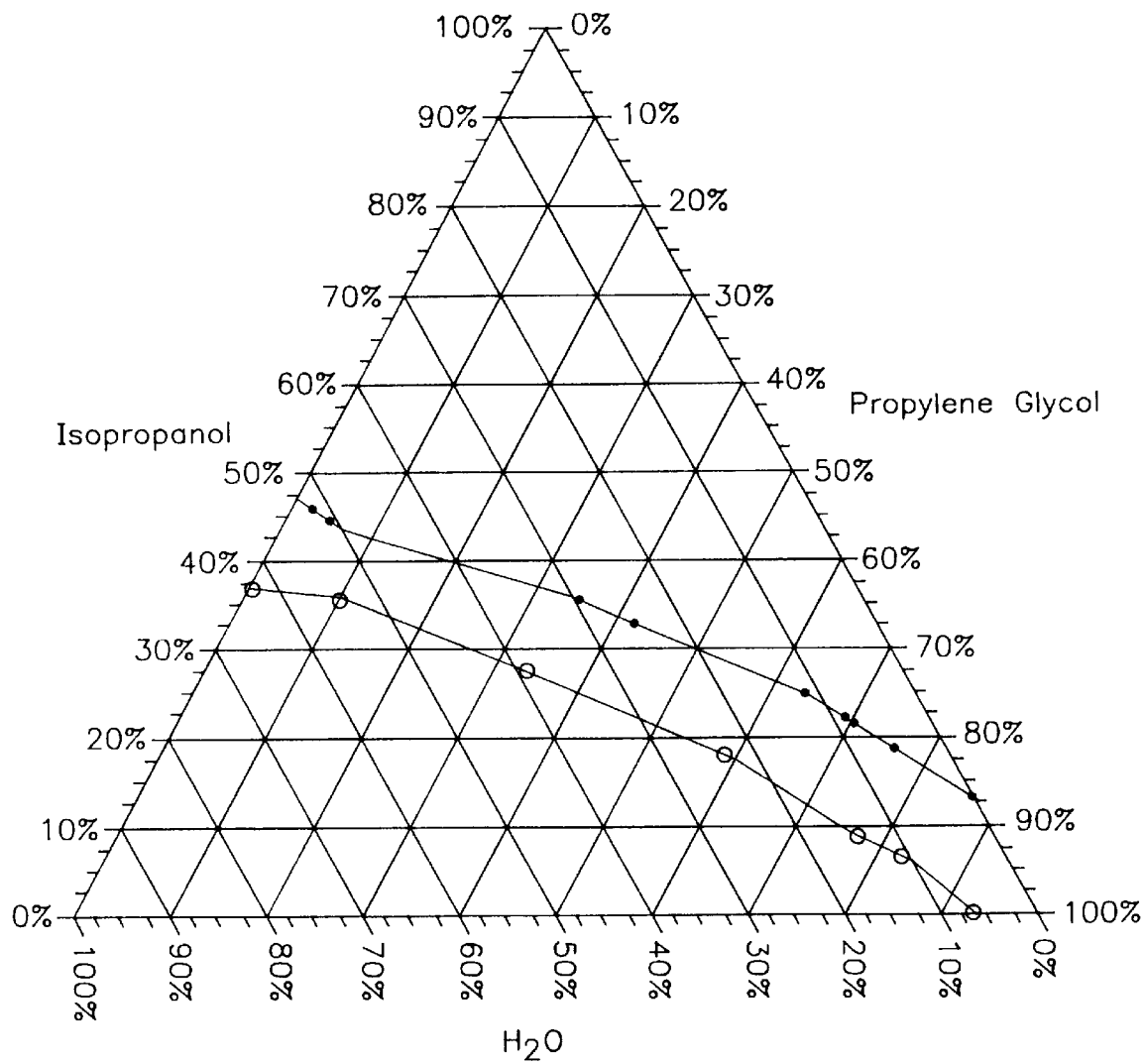
FIG. 2 is a ternary phase diagram showing the miscibility of the 1,3-dioxolane skin penetration enhancer at 10 wt. % (■) or 2 wt. % (○) in an isopropanol-propylene glycol-water vehicle.

Accordingly, the vehicle or carrier system for the NSAID and enhancer components is preferably an aqueous or non-aqueous alcoholic carrier containing sufficient alcohol, especially ethanol and/or isopropanol and, often, glycol, e.g., propylene glycol, to solubilize the NSAID and be miscible with the enhancer. Generally, however, depending on the amounts of enhancer and NSAID in the formulations the aqueous alcoholic carrier can contain from about 35% to about 70% of ethyl alcohol and/or isopropyl alcohol, preferably, from about 50 to about 70 percent of ethanol or from about 45 to 55 percent of isopropanol. Mixtures of ethanol and isopropanol in proportions providing the desired solubility of NSAID and compatibility with the enhancer can also be used. More generally, however, the present inventors have developed miscibility data for combinations of alcohol (ethanol or isopropanol), glycol (propylene glycol) and water for the enhancer (2-n-nonyl 1,3-dioxolane). This data is graphically represented by the ternary phase diagrams provided as FIG. 1 (for ethanol) at 2 wt. % (●) and 10 wt. % (■) of the enhancer compound and FIG. 2 (for isopropanol) at 2 wt. % (○) and 10 wt. % (●) of the enhancer compound. In each of these phase diagrams, the upper portions (above the lines connecting the data points) represent the proportions at which the vehicle components are miscible with each other and with the enhancer; conversely, the region below the lines connecting the data points represent the proportions where the vehicle components are immiscible.

Again, the total amount of the aqueous or non-aqueous, alcoholic carrier will depend on the amount of NSAID, amount and type of enhancer, and the form of the composition, e.g., gel, cream, ointment, etc. Usually amounts of the aqueous or non-aqueous alcoholic carrier within the range of from about 70% to about 95% may be used.

In the preferred compositions which are in the form of a gel, a thickening agent, such as hydroxypropyl cellulose, will be included as a gelling agent. However, any other pharmaceutically acceptable thickening/gelling agent may be used. For example, mention may be made of other cellulosic ethers, polymeric thickening agents, e.g., acrylic acid polymers, Carbopol® thickeners, etc., xanthan gum, guar gum, and the like, as well as inorganic thickeners/gelling agents. The amount of the thickening agent is not particularly critical and can be selected to provide the desired product consistency or viscosity to allow for easy application to the skin but which will not be too watery or loose so that it will stay where applied. Generally, depending on its molecular weight, amounts of thickening agent up to about 5%, such as, for example, from 0.1 to about 2%, of the composition will provide the desired effect.

As also well known in this art, it is possible to include other ingredients in the formulations for particular aesthetic and/or functional effects. For example, the formulations may, optionally, include one or more moisturizers for hydrating the skin and emollients for softening and smoothing the skin. Glycerin is an example of such a suitable moisturizing additive. When present the additive will usually be incorporated in an amount of up to about 5 percent by weight of the composition, for example, from about 0.1 to 5%.

The effects of the topical compositions according to the invention are further illustrated by way of the following representative examples which in no way are intended to limit the scope of the invention.

EXAMPLE 1

This example compares the percutaneous absorption through porcine skin, of ibuprofen from aqueous alcoholic gels containing 5 wt. % ibuprofen and either 5%, 10% or 15% of 2-n-nonyl-1,3-dioxolane, using an ethanol/water carrier at a 70:30 mixing ratio. The formulations include NaOH to adjust the pH to 7.4, but do not include a glycol. Hydroxypropyl cellulose (2 wt. %) is used as the gelling agent. The test compositions are applied to provide about 30 milligrams (mg) of the composition per square centimeter ($cm^2$) of porcine skin.

The tests are run in standard static cells with phosphate buffered saline (PBS) as the receptor fluid (surface area 0.635 $cm^2$, temperature 32° C.). The following Table 1 shows the total amount of ibuprofen applied to the skin for each formulation. The differences result from the slightly different thicknesses at which the test formulations are applied. Each test was run for 24 hours under non-occluded conditions with the finite dose of the test formulation.

TABLE 1

| Enhancer | Amount of Enhancer (wt. %) | Total Amount of Ibuprofen applied to skin sample ($\mu$g) per 0.635 $cm^2$ cell |
|---|---|---|
| 2-n-nonyl-1,3-dioxolane | 5 | 988 |
| 2-n-nonyl-1,3-dioxolane | 10 | 1051 |
| 2-n-nonyl-1,3-dioxolane | 15 | 1038 |

The results are obtained and reported in Table 2 as the average values for six (6) cells (samples). The initial flux over the first two hours was significantly higher for each formulation containing the 1,3-dioxolane, but especially at the higher level (15%, maximum flux about 8.5 $\mu$g/$cm^2$/hr; 5% and 10%, maximum flux about 4 $\mu$g/$cm^2$/hr) of the enhancer. The flux tended to even out after 4 to 6 hours and continued at about the same level for at least about 24 hours. The results for total amount of ibuprofen vs. time (flux); and the payout of ibuprofen at 24 hours, total and percent of dose, are shown in the following Table 2:

TABLE 2

| | Flux ($\mu$g/$cm^2$/hr) | | | | Delivery at 24 h | |
|---|---|---|---|---|---|---|
| Amount Enhancer (%) | 2 h | 4 h | 6 h | 24 h | Total ($\mu$g) | % of Dose |
| 5 | 4 | 2 | 1.5 | 1 | 20.2 ± 6.9 | 2.1 ± .7 |
| 10 | 4 | 2 | 1.5 | 1.5 | 26.6 ± 8.1 | 2.4 ± .6 |
| 15 | 8 | 4 | 3.5 | 3.5 | 57.7 ± 33.4 | 5.4 ± 2.5 |

When the procedure of Example 1 was repeated but using 5%, 10% or 15% of Azone™, the initial flux at 2 hours and 4 hours was only between about 1 to 1.5 $\mu$g/$cm^2$/hr.

EXAMPLE 2

This example shows the effect of incorporating propylene glycol in the aqueous alcoholic gel formulation containing 5% ibuprofen and 10% 2-n-nonyl-1,3-dioxolane using an ethanol:water vehicle at a 70:30 weight mixing ratio. The compositions used in these tests are shown in Table 3 (NaOH is added to adjust the pH to 7.4):

TABLE 3

| | ibuprofen (%) | enhancer (%) | propylene glycol (%) | Ethanol (%) | Water (%) | Total (%) |
|---|---|---|---|---|---|---|
| A | 5 | 10 | 0 | 59.5 | 25.5 | 100 |
| B | 5 | 10 | 5 | 56 | 24 | 100 |
| C | 5 | 10 | 10 | 52.5 | 22.5 | 100 |
| D | 5 | 10 | 15 | 49 | 21 | 100 |
| E | 5 | 10 | 20 | 45.5 | 19.5 | 100 |

Figure 3:
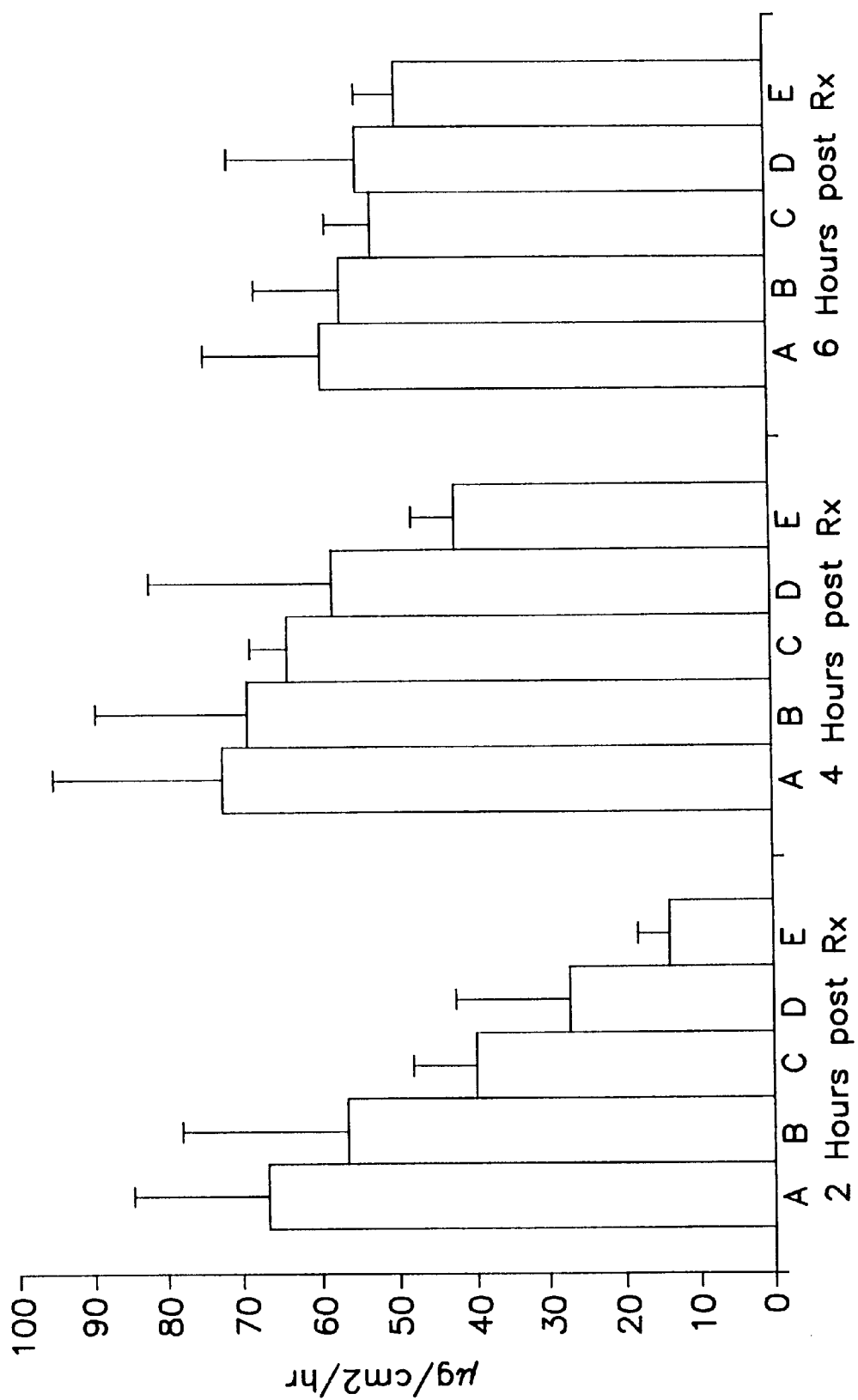
FIG. 3 is a bar graph plotting the flux of ibuprofen Na in an in vitro study as a function of time at 2, 4 or 6 hours post topical application for formulations containing 5% ibuprofen and 0% (bar A), 5% (bar B), 10% (bar C), 15% (bar D) or 20% (bar E) of propylene glycol in an aqueous-alcoholic (ethanol) gel formulation.

The test was run using the same conditions as described in Example 1. The flux was measured at 2, 4 and 6 hours. The results are shown graphically in FIG. 3. From this figure it is seen that the flux at 2 hours decreases nearly linearly as the propylene glycol (PG) content increases from 0% to 5% to 10% to 15% to 20%. At four hours after the composition is applied to the test skin sample the fluxes for each concentration of PG has increased but more so for the compositions containing the higher amounts of PG. Finally, at 6 hours the fluxes begin to even out.

This example, therefore, shows that only low or no propylene glycol should be included in the ibuprofen topical composition using the 2-substituted-1,3-dioxolane, 2-substituted-1,3-dioxane or substituted acetal as the penetration enhancer where the goal is to administer large quantity of active ingredient as quickly as possible such that relief from pain or inflammation can begin rapidly, for example in the treatment of sunburn or other burn injury or for relief of muscular pain caused by inflammation. However, over the longer period of time essentially the same amount of ibuprofen is percutaneously delivered at each amount of propylene glycol.

EXAMPLE 3

This example is similar to Example 1 but compares a topical aqueous alcoholic gel formulation with ibuprofen according to the present invention with a similar gel but without the enhancer and with four other commercially available topical ibuprofen formulations. Also, human skin was used rather than porcine skin. The composition according to the present invention and the comparison were as follows:

| Ingredient | Invention Amount (wt. %) | Comparison Amount (wt. %) |
|---|---|---|
| Ibuprofen | 5 | 5 |
| 2-n-nonyl-1,3 dioxolane | 10 | 0 |
| Ethanol | 59 | 65 |
| Propylene glycol | 17 | 19 |
| Water | 7 | 9 |
| Hydroxypropyl cellulose | 2 | 2 |
| Sodium Hydroxide | q.s. to pH 7 | q.s. to pH 7 |

The commercially available products were: Gelufene® (ibuprofen 5%, isopropyl alcohol, hydroxyethylcellulose, sodium hydroxide, benzyl alcohol and purified water), Dolgit® cream (ibuprofen 5%, medium chain triglycerides, mixture of glycerol monostearate and polyoxyethylene stearates, polyoxyethylene fatty acid esters, xanthan gum, lavender oil, neroli oil, water, propylene glycol, parahydroxybenzoate of methyl soda), Ibutop® (ibuprofen 5%) (Laboratoire Chefaro-Ardeval, Saint-Denis Cedex, France) and Deep Relief™ gel (ibuprofen 5%, menthol, Carbomer, propylene glycol, di-isopropanolamine, ethanol, purified water).

Figure 5:
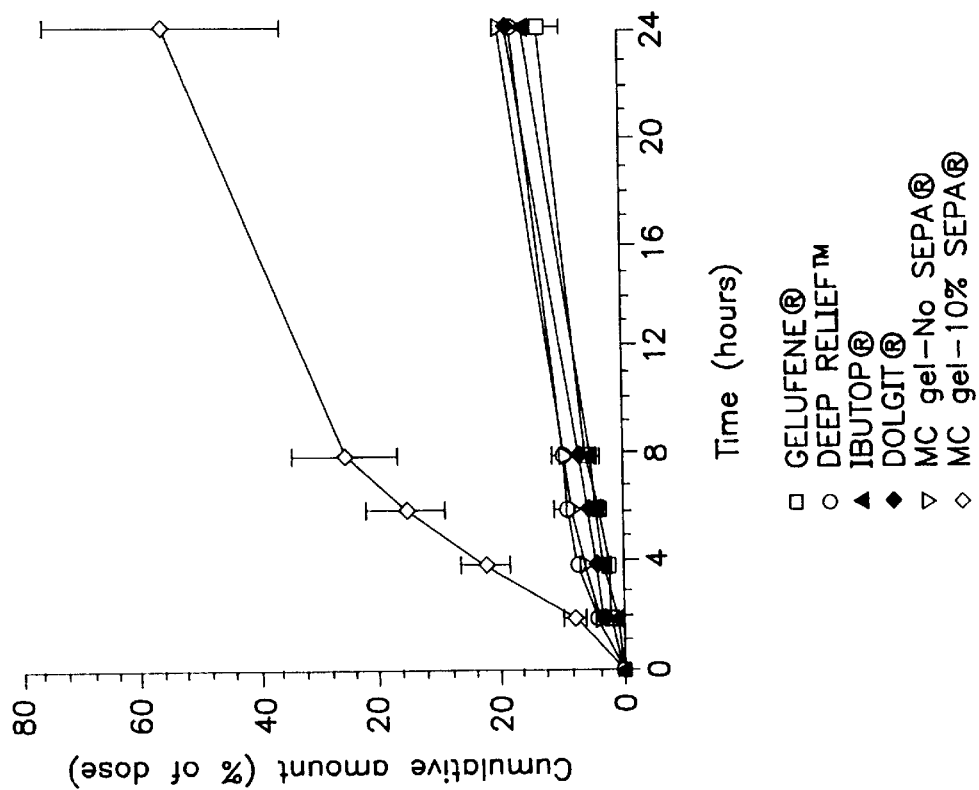
FIG. 5 is a graph plotting cumulative diffusion of ibuprofen Na versus time for the same samples used in the study of FIG. 4.
Figure 4:
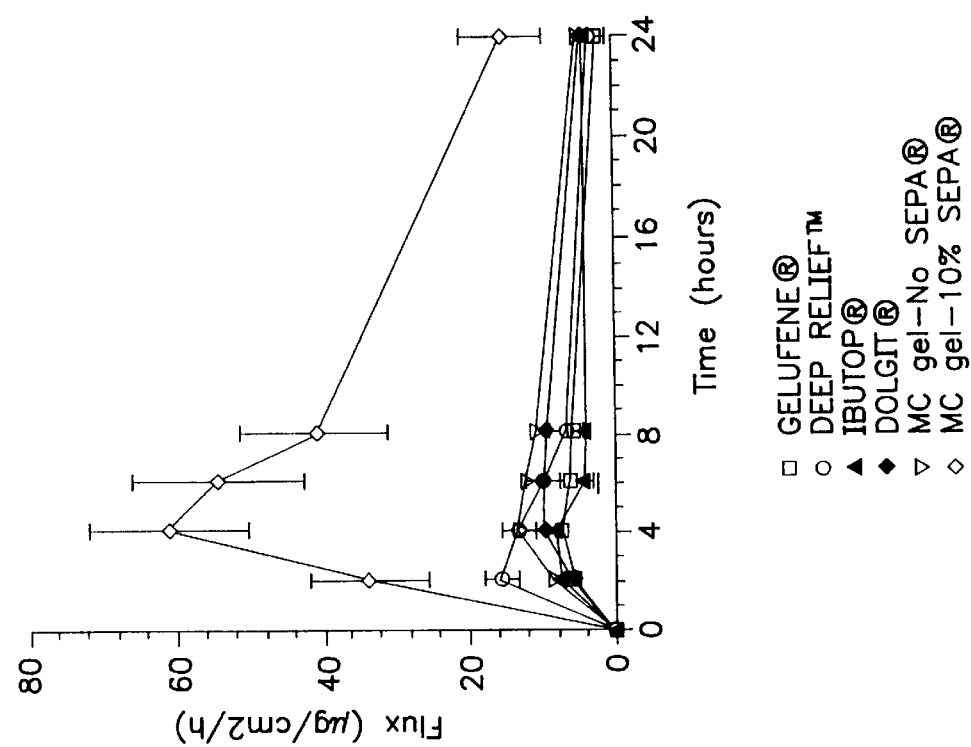
FIG. 4 is a graph plotting flux of ibuprofen Na versus time in an in vitro study (Example 3) for an aqueous alcoholic gel according to the invention and containing 10 wt. % of 2-n-nonyl-1,3-dioxolane skin penetration enhancer (◇), or a similar gel without skin penetration enhancer (▽), or for four commercial topical ibuprofen preparations: Gelufene® (□), Deep Relief™ (○), Ibutop® (△) and Dolgit® (◆)

The results are shown in FIG. 4 for flux versus time and in FIG. 5 for cumulative diffusion of ibuprofen through the skin sample. The initial flux and cumulative amount of the ibuprofen are both significantly higher for the invention formulation than for the control or commercial products.

EXAMPLE 4

This Example is also similar to Example 1 but is designed to compare the percutaneous absorption through porcine skin of ibuprofen (as the sodium salt) from 5% ibuprofen formulations containing 10% 2-n-nonyl-1,3-dioxolane with 5%, 10%, 15% or 20% propylene glycol (PG) or 20% isopentyldiol (IP). The test conditions were otherwise the same as used in Example 1. The formulations tested are shown in Table 4:

TABLE 4

| Run No. | Ibuprofen (%) | Enhancer (%) | glycol PG or IP (%) | EtOH (%) | Water (%) | Total (%) |
|---|---|---|---|---|---|---|
| 1 | 5 | 10 | 0 PG | 59.5 | 25.5 | 100 |
| 2 | 5 | 10 | 5 PG | 58.9 | 21.1 | 100 |
| 3 | 5 | 10 | 10 PG | 58.3 | 16.7 | 100 |
| 4 | 5 | 10 | 15 PG | 57.6 | 12.4 | 100 |
| 5 | 5 | 10 | 20 PG | 56.9 | 8.1 | 100 |
| 6 | 5 | 10 | 20 IP | 56.9 | 8.1 | 100 |

Figure 7:
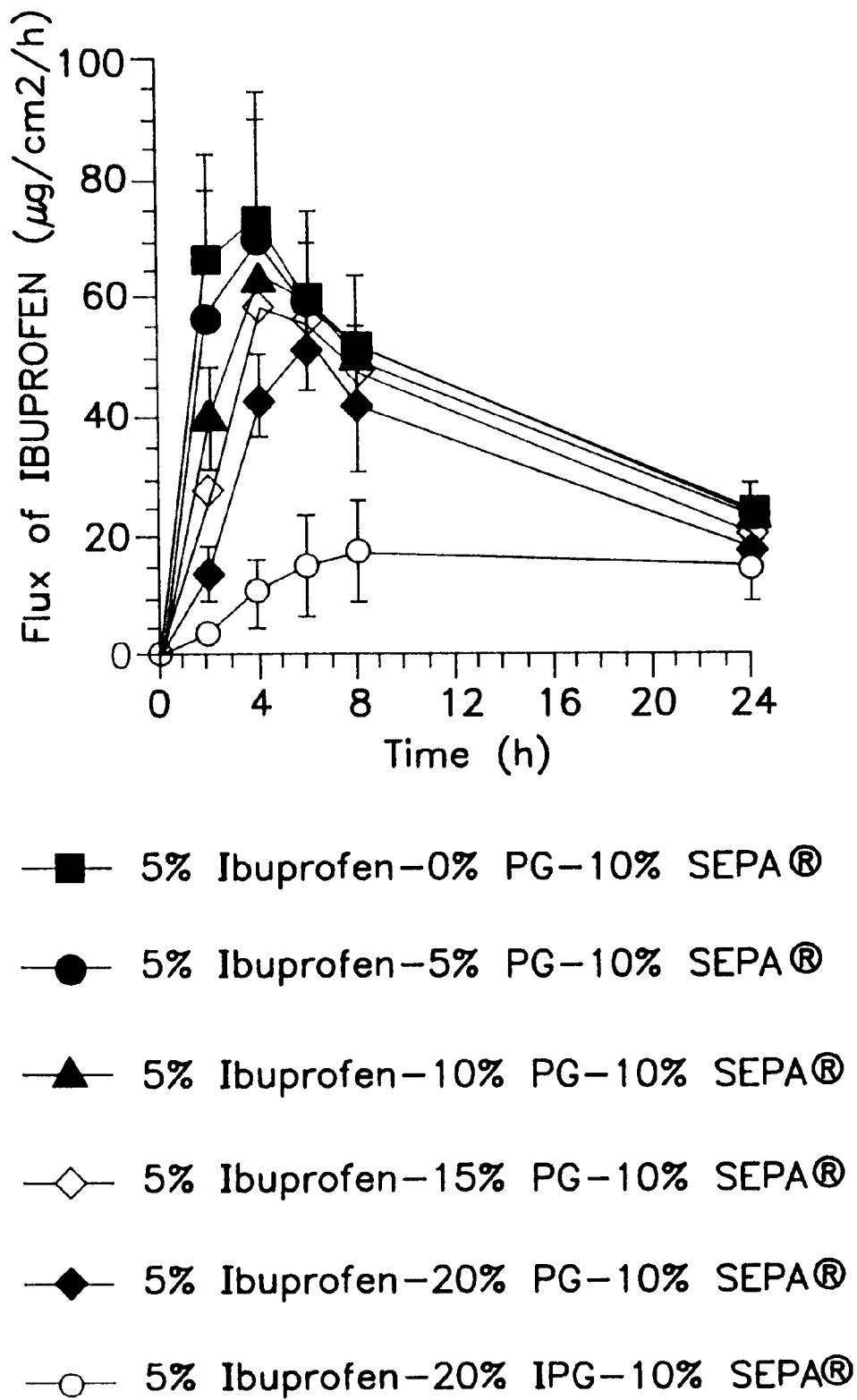
FIG. 7 is a graph plotting flux of ibuprofen Na versus time in the in vitro study of Example 4 for aqueous alcoholic gels containing 5 wt. % ibuprofen, sodium, 10 wt. % of 2-n-nonyl-1,3-dioxolane skin penetration enhancer and 0% propylene glycol (PG) (■), 5 wt. % PG (●), 10 wt. % PG (▲), 15 wt. % PG (◇), 20 wt. % PG (◆) or 20 wt. % isopentyldiol (IP) (○).

The flux of ibuprofen in the receptor cell was measured and the results are shown in FIG. 7. In this case, the peak flux was reached for the formulations of Run Nos. 1–4 within four hours after application and reached values in the range of from about 60 to 72 $\mu g/cm^2/hr$. For the 20% PG formulation (run #5) the peak flux was reached at 6 hours and was about 50 $\mu g/cm^2/hr$. For the 20% IP formulation (run #6) the peak flux was only about 16 $\mu g/cm^2/hr$ and was not reached until 8 hours after application.

The following Table 5 shows the results reported for the cumulative amount of ibuprofen reaching the receptor cell after 24 hours, and the amount reaching the receptor cell as a age (%) of the dose applied after 24 hours.

TABLE 5

| | | Delivery at 24 h | |
|---|---|---|---|
| Run | PG or IP (wt. %) | Total ($\mu$g) | % Dose |
| 1 | 0 | 541.7 ± 4.8 | 60.1 ± 8.6 |
| 2 | 5 PG | 519.8 ± 53.7 | 57.9 ± 5.7 |
| 3 | 10 PG | 498.6 ± 58.9 | 56.5 ± 6.6 |
| 4 | 15 PG | 443.5 ± 105.1 | 50.1 ± 11.4 |
| 5 | 20 PG | 358.5 ± 73.5 | 40.7 ± 8.4 |
| 6 | 20 IP | 144.5 ± 31.1 | 16.6 ± 3.6 |

EXAMPLE 5

This is example is designed to demonstrate the effect of concentration of ibuprofen (IB) on flux and total delivery (24 h) for formulations with and without propylene glycol. The test were run under the same conditions as in Example 1 except that human skin was used, an 80/20 mixture of PBS and ethanol was used as the receptor fluid, and the pH was adjusted to 7.7 with sodium hydroxide; the test compositions which were prepared and tested (the enhancer was 2-n-nonyl-1,3-dioxolane) are shown in the following Table 6:

TABLE 6

| Run No. | Ibuprofen (%) | Enhancer (%) | PG (%) | EtOH (%) | Water (%) | Total (%) |
|---|---|---|---|---|---|---|
| 1 | 2.5 | 10 | 17.5 | 61.25 | 8.75 | 100 |
| 2 | 5 | 10 | 17 | 59.5 | 8.5 | 100 |
| 3 | 10 | 10 | 16 | 56 | 8 | 100 |
| 4 | 2.5 | 10 | — | 61.25 | 26.25 | 100 |
| 5 | 5 | 10 | — | 59.5 | 25.5 | 100 |
| 6 | 10 | 10 | — | 56 | 24 | 100 |

Figure 8:
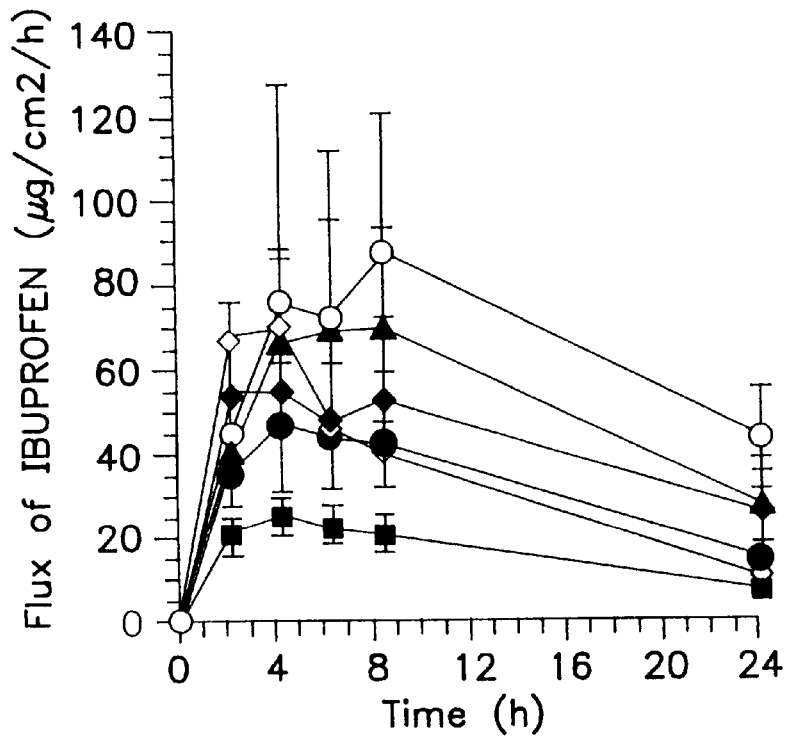
FIG. 8 is a graph plotting flux of ibuprofen Na versus time in the in vitro study of Example 5 for aqueous alcoholic gels containing 10 wt. % of penetration enhancer and either 2.5 wt. % ibuprofen, sodium with (■) or without (◇) propylene glycol (PG); 5 wt. % IB with (●) or without (◆) propylene glycol; and 10 wt. % IB with (▲) or without (○) propylene glycol.

The flux as a function of time for each of the test formulations is shown in FIG. 8. comparing the results for Run Nos. 1 and 4, Run Nos. 2 and 5 and Run Nos. 3 and 6, it is seen that in each case the maximum (peak) flux and time to reach peak flux were higher and quicker for the formulations without propylene glycol.

The results for the cumulative dose of ibuprofen at 24 hours and the percentage of the original dose passing through the skin at 24 hours are shown in the following Table 7:

TABLE 7

| | | Delivery at 24 h | |
|---|---|---|---|
| Run | PG(wt %)/IB(wt %) | Total ($\mu$g) | % Dose |
| 1 | 17.5/2.5 | 193.5 ± 37.3 | 37.6 ± 6.5 |
| 2 | 17/5 | 361.9 ± 116.3 | 38.2 ± 12.7 |
| 3 | 16/10 | 615.2 ± 152.6 | 29.8 ± 7.5 |
| 4 | 0/2.5 | 392.2 ± 189.1 | 80.4 ± 30.2 |
| 5 | 0/5 | 535.7 ± 189.1 | 53.6 ± 19.9 |
| 6 | 0/10 | 805.9 ± 214.4 | 41.2 ± 8.8 |

These results show, for example, that the formulation with 10% ibuprofen but without propylene glycol (Run No. 6) gives the highest flux. Furthermore, the formulation of Run No. 4 (2.5 g IB per 100 g formula+0 PG) will deliver 80 mg of ibuprofen over a 100 $cm^2$ area.

EXAMPLE 6

Figure 6:
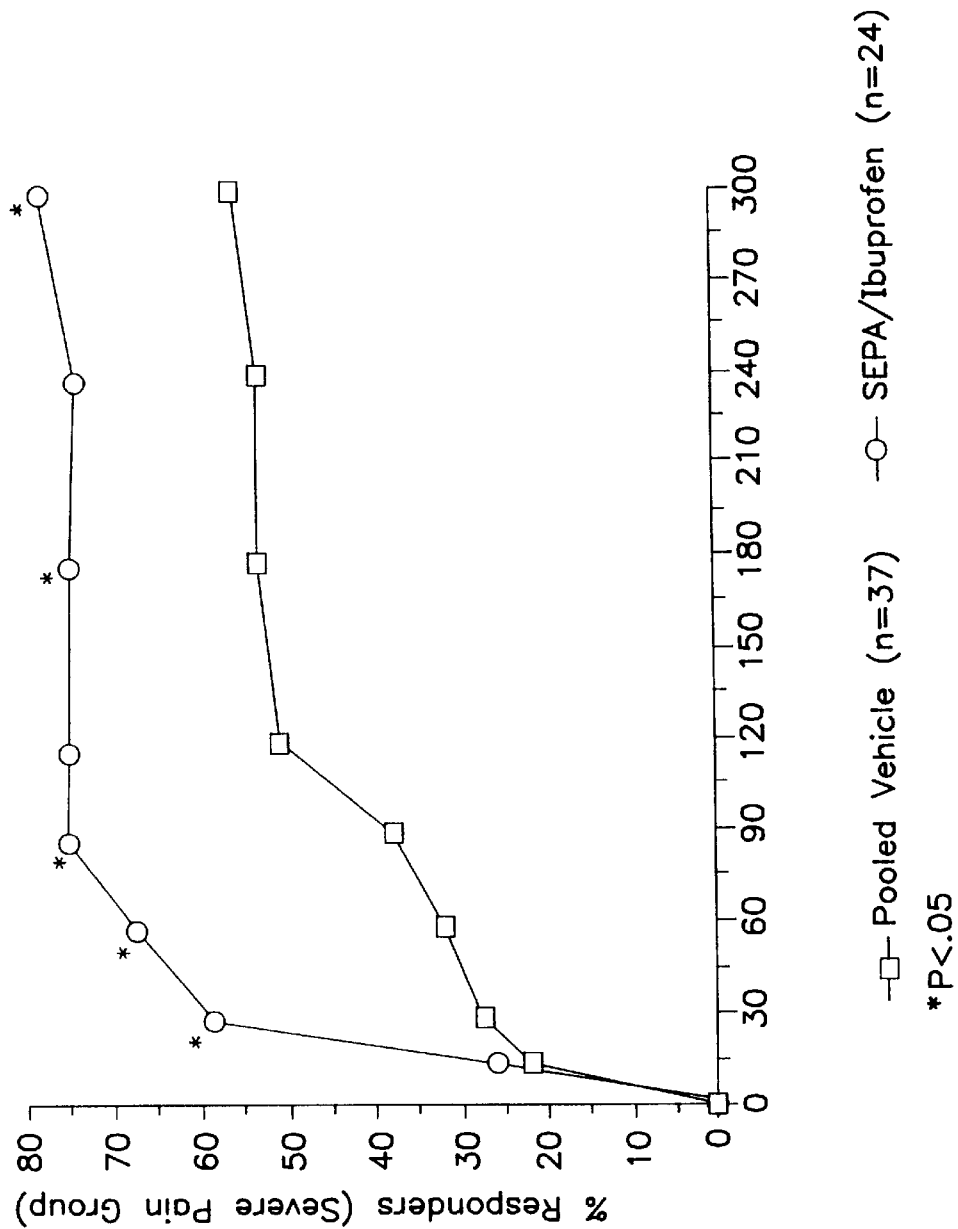
FIG. 6 is a graph plotting the number (percentage) of respondents reporting pain relief as a function of time (minutes) in a clinical trial as described in Example 6 using either a formulation according to this invention (○) or a pooled vehicle (□).

This example shows the results of a clinical study on human patients experiencing severe pain. The same formulation as shown in Example 3 (10% 2-nonyl-1,3-dioxolane and 5% ibuprofen and 17% propylene glycol) is used in these studies. As control, a pooled vehicle (mixture of first formulation with no drug and no enhancer and second formulation with no drug but with enhancer) was similarly tested. The results are shown in FIG. 6.

EXAMPLE 7

This Example compares percutaneous absorption through human skin of Naproxen Na from various formulations containing 5% (w/w) Naproxen gels with or without propylene glycol and with or without skin penetration enhancer compound (2-n-nonyl-1,3-dioxolane). The tests were run under the same conditions described in Example 5 (pH=7.7) using the gel formulations as shown in Table 8:

TABLE 8

| Run No. | Naproxen (%) | Enhancer (%) | PG (%) | EtOH (%) | Water (%) | Total (%) |
|---|---|---|---|---|---|---|
| 1 | 5 | 0 | — | 66.5 | 28.5 | 100 |
| 2 | 5 | 5 | — | 63 | 27 | 100 |
| 3 | 5 | 10 | — | 59.5 | 25.5 | 100 |
| 4 | 5 | 0 | 19 | 66.5 | 9.5 | 100 |
| 5 | 5 | 5 | 18 | 63 | 9 | 100 |
| 6 | 5 | 10 | 17 | 59.5 | 8.5 | 100 |

With these Naproxen gel formulations the highest flux and highest total delivery was achieved with the formulation of Run No. 2 (0% PG+5% enhancer). The peak flux was observed 4 hours after application of the gel on the skin.

The results for the cumulative dose of naproxen at 24 hours and the percentage of the original dose passing through the skin at 24 hours are shown in the following Table 9:

TABLE 9

| | | Delivery of Naproxen Na at 24 h | |
|---|---|---|---|
| Run | PG(wt %)Enhancer(wt %) | Total (µg) | % Dose |
| 1 | 0/0 | 51.5 ± 16.6 | 5.2 ± 1.4 |
| 2 | 0/5 | 499.0 ± 96.9 | 52.3 ± 10.9 |
| 3 | 0/10 | 369.1 ± 74.8 | 35.9 ± 7.5 |
| 4 | 19/0 | 29.4 ± 12.4 | 2.9 ± 1.1 |
| 5 | 18/5 | 149.5 ± 40.3 | 15.0 ± 4.0 |
| 6 | 17/10 | 409.6 ± 113.8 | 39.7 ± 12.3 |

These results appear to show that propylene glycol is not functioning as an enhancer in the subject formulations (compare, e.,g., run No. 1 with Run No. 4) and further, propylene glycol has an adverse impact on the delivery of the NSAID, Naproxen.

EXAMPLE 8

This example illustrates the effect of propylene glycol (PG) on delivery of various NSAIDs from aqueous formulations containing 10 wt. % of skin penetration enhancer, 2-n-nonyl-1,3-dioxolane. All the tested formulations included ethanol and water at a 70:30 weight ratio and were neutralized with base to a pH of about 7. The tests were run in standard static cells under substantially the same conditions as described in Example 1 but using human skin rather than procine skin. The tested compositions and results are shown in the following Table 10.

TABLE 10

| NSAID Drug | Drug conc. | % enhancer | % PG | Avg 24 Hour % Dose |
|---|---|---|---|---|
| Ketoprofen | 2.5% | 10 | 0 | 9.1 |
| | | 10 | 5 | 10.3 |
| | | 10 | 10 | 12.0 |
| | | 10 | 20 | 27.0 |
| Piroxicam | 0.5% | 10 | 0 | 66.3 |
| | | 10 | 10 | 55.1 |
| | | 10 | 20 | 63.5 |
| Ibuprofen | 5% | 10 | 0 | 61.7 |
| | | 10 | 5 | 57.9 |
| | | 10 | 10 | 56.5 |
| | | 10 | 15 | 50.1 |
| | | 10 | 20 | 28.3 |
| Diclofenac | 1% | 10 | 0 | 18.7 |
| | | 10 | 5 | 29.7 |
| | | 10 | 10 | 35.3 |
| | | 10 | 20 | 45.2 |
| Ketorolac | 1% | 10 | 0 | 10.8 |
| | | 10 | 5 | 27.1 |
| | | 10 | 10 | 25.0 |
| | | 10 | 20 | 19.3 |
| Naproxen | 5% | 10 | 0 | 35.9 |
| | | 10 | 20 | 39.7 |

As may be readily ascertained from these results the effects of propylene glycol differs substantially from one NSAID to another. The effect, in terms of total delivery (reported as percent of original dose) at twenty four hours) of NSAID is positive for ketoprofen and diclofenac; substantially neutral for piroxican and naproxen; negative for ibuprofen (particularly at the high levels of propylene glycol); and intermediate for ketorolac.

EXAMPLE 9

This example further illustrates the effects of PG on drug delivery (0.5% piroxicam) at two different levels of the enhancer, 2-n-nonyl-1,3-dioxolane (5% or 10%) versus a control (0% enhancer, 0% PG) and a commercial product, Geldene® (0.5% piroxicam in the form of its diisopropanolamine (DIPA) salt; approximately 24% ethanol; >0 PG). In the compositions according to the invention and the control triethanolamine (TEA) was used as the base to neutralize the piroxicam and the vehicle was ethanol:water (70:30). The formulations and test procedures were, otherwise, as described in Example 8. The results are shown below in Table 11.

TABLE 11

| Run No. | Propylene Glycol (wt %) | Enhancer (wt. %) | Peak Flux µg/cm$^2$/h | % of Dose 24 h |
|---|---|---|---|---|
| 9-1 | 0 | 10 | 8.7 | 66 |
| 9-2 | 10 | 10 | 8.5 | 55 |
| 9-3 | 20 | 10 | 9.8 | 64 |
| 9-4 | 0 | 5 | 7.0 | 54 |
| 9-5 | 10 | 5 | 6.4 | 46 |
| 9-6 | 20 | 5 | 6.6 | 47 |
| 9-7 (control) | 0 | 0 | 3 | 11 |
| 9-8 (Gelden ®) | >0 | — | 2 | 13 |

From these results it is observed that PG has little or no effect on drug delivery at either 5% or 10% of enhancer. However, all the formulations with enhancer provide significantly higher peak and total drug delivery than either the control or the commercial product. There is no significant different in performance between the control and the commercial product.

EXAMPLE 10

This example further illustrates the effects of the invention with diclofenac as the NSAID. The test procedure was substantially the same as previously described using either human (H) or porcine (P) skin and an ethanol:water (70:30) vehicle. 2-n-nonyl-1,3-dioxolane was used as the skin permeation enhancer compound according to the invention. The results are shown in Table 12 below. In Run Nos. 10-A through 10-G 1 wt. % of diclofenac (as free acid) was used. In Run Nos. 10-I and 10-J (commercial product) 0.93 wt. % of diclofenac (as free acid) was used.

TABLE 12

| Run No. | Base | PG(%) | Enhancer (%) | Skin | Peak Flux $\mu g/cm^2/h$ | % of dose 24 h |
|---|---|---|---|---|---|---|
| 10-A | Na | 20 | 10 | P | 12 | 40 |
| 10-B | Na | 10 | 10 | P | 10 | 36 |
| 10-C | Na | 5 | 10 | P | 6 | 30 |
| 10-D | Na | 20 | 5 | P | 8 | 28 |
| 10-E | Na | 0 | 10 | P | 2.5 | 19 |
| 10-F | Na | 20 | 0 | P | 1 | 8 |
| 10-G | DEA[b] | 20 | 10 | H | 15 | 76 |
| 10-H | Na | 20 | 10 | H | 10 | 46 |
| 10-I | DEA | 20 | 10 | H | 11 | 46 |
| 10-J[a] | DEA | — | — | H | 1.5 | 10 |

[a]Emugel (Voltaren)
[b]diethylamine

From the above results reported in Table 12 the following observations and conclusions may be drawn. The first set of experiments, Run Nos. 10A–10C, show that PG exerts a positive effect as a co-enhancer for diclofenac. In a second set of experiments Run Nos. 10D–10F, it is seen that the combination of PG with the dioxolane enhancer provides better performance than might be expected from the results with dioxolane enhancer alone and with PG alone. From the third set of experiments, Run Nos. 10-G and 10-H, it is observed that DEA as the counterion (base) provides better performance than sodium (Na). Finally, from the fourth set of experiments, Run Nos. 10-I and 10-J it is seen that the formulation according to the present invention provides significantly improved performance in comparison to a commercial diclofenac topical formulation.

EXAMPLE 11

This example shows the effects of multiple daily applications of a formulation according to the invention (10% 2-n-nonyl-1,3-dioxolane, 20% PG, 70:30 EtOH/H$_2$O) and a commercial topical NSAID formulation (Emulgel). Each product was applied to human skin sample with second and third applications following at 8 hour intervals. The results are shown below in Table 13.

TABLE 13

| Run No. | Peak Flux $\mu g/cm^2/h$ | $\mu g$ at 24 h |
|---|---|---|
| 11-A (Diclofenac,Na,0.93%) | | |
| 1st Application (0 h) | 13 | 125 |
| 2nd Application (8 h) | 11 | 230 |
| 3rd Application (16 h) | 18 | 360 |
| 11-B (Emulgen,Diclofenac,0.93%) | | |
| 1st Application (0 h) | 9 | 100 |
| 2nd Application (8 h) | 4 | 100 |
| 3rd Application (16 h) | 10 | 130 |

Accordingly, it is seen that a single application of the topical diclofenac formulation according to the present invention provides comparable performance to 3 applications of the commercial diclofenac topical formulation. Whereas, 3 daily applications of the topical NSAID formulation of this invention provides nearly a three-fold higher delivery of drug than 3 applications of the commercial product while a two-fold improvement in drug delivery is obtained with 2 daily applications of the invention product as compared to 2 daily applications of the commercial product.

What is claimed is:

1. A substantially neutral ibuprofen containing alcoholic or aqueous alcoholic composition which comprises, on a weight basis, of the total composition:

a therapeutically effective amount, in the range of from about 2 to 10% ibuprofen in the form of its pharmacologically acceptable salt;

a skin penetration enhancing effective amount in the range of from about 4 to 15% of a $C_7$ to $C_{14}$-hydrocarbyl substituted 1,3-dioxolane, 1,3-dioxane or acetal;

0 to about 18% of glycol having from 3 to 6 carbon atoms;

at least about 40% of volatile alcohol selected from the group consisting of ethanol, isopropanol and mixture thereof;

0 to about 25% water;

base to provide a pH in the range of from 6.5 to about 8, and, optionally, gelling agent effective to thicken the composition to avoid or minimize run-off when applied to the skin.

2. The composition according to claim 1 which comprises from about 2 to about 10% said salt of ibuprofen;

from about 4 to about 15% of the enhancer wherein the alkyl group substituent has from about 7 to about 10 carbon atoms;

from about 0 to about 15% propylene glycol;

from about 55 to about 70% ethanol;

from about 4 to about 25% water;

base in amount to adjust the pH of the composition in the range of from 6.5 to about 7.5, and, 0 to about 2% of gelling agent.

3. A glycol-free topical composition effective for the transdermal administration of naproxen, which comprise, on a weight basis of the total composition:

a pharmaceutically effective amount of naproxen, from about 2 to about 20% of 2-$C_7$–$C_{14}$ hydrocarbyl substituted 1,3-dioxolane, 1,3-dioxane, or acetal skin penetration enhancer;

from about 35 to about 85% ethanol, iso-propanol, or mixture thereof;

0 to about 40% water;

base in an amount to provide a pH in the range of from about 6 to about 8, and up to about 5% gelling agent.

4. A method for the transdermal administration of ibuprofen to a patient in need thereof which comprises topically applying to the skin of the patient a substantially neutral composition comprising from about 5 to about 15 weight percent of ibuprofen in the form of its pharmacologically acceptable salt in a vehicle comprising a lower alcohol selected from the group consisting of ethanol, isopropanol and mixture thereof, alkyl glycol having from 3 to 6 carbon atoms, and water in a mixing ratio of alcohol:glycol:water of 40–80:0–20:0–25, said vehicle comprising from about 70 to about 90 weight percent of the composition, and from about 5 to about 15 weight percent of a skin penetration enhancing compound selected from the group consisting of 2-hydrocarbyl-1,3-dioxolane, 2-hydrocarbyl-1,3-dioxane and hydrocarbyl substituted-acetal, wherein the hydrocarbyl group has from 7 to 14 carbon atoms, and base in amount to provide a pH in the range of from 6.5 to about 8.

5. A method for the transdermal administration of naproxen to a patient in need thereof which comprises topically applying to the skin of the patient a substantially neutral composition comprising a therapeutically effective amount of naproxen in a glycol-free vehicle comprising a lower alcohol selected from the group consisting of ethanol, isopropanol and mixture thereof, and water in a mixing ratio of alcohol:water of 35–85:10–40, said vehicle comprising from about 70 to 90 weight percent of the composition, and from about 2 to 20 weight percent of a skin penetration enhancing compound selected from the group consisting of 2-hydrocarbyl-1,3-dioxolane, 2-hydrocarbyl-1,3-dioxane and hydrocarbyl substituted-acetal, wherein the hydrocarbyl has from 7 to 14 carbon atoms, and base in amount to provide a pH in the range of from 6.5 to about 8.

6. The composition according to claim 2 which comprises from about 2 to about 10% said salt of ibuprofen;

from about 5 to about 10% of the enhancer;

about 0% propylene glycol;

from about 55 to about 70% ethanol;

from about 4 to about 25% water;

base in amount to adjust the pH of the composition to from 6.5 to about 7.5; and 0 to 2% gelling agent.

7. The composition according to claim 2 which comprises from about 2 to about 10% said salt of ibuprofen;

from about 5 to about 10% of the enhancer;

from about 1 to about 15% propylene glycol;

from about 55 to about 70% ethanol;

from about 4 to about 25% water;

base in amount to adjust the pH of the composition to from 6.5 to about 7.5; and 0 to about 2.0% gelling agent.

8. The glycol-free composition of claim 3 wherein the amount of enhancer is from about 5 to about 10%.

9. The composition of claim 2 which comprises about 5% of said salt of ibuprofen;

from about 5 to about 10% skin penetration enhancer wherein the hydrocarbyl group substituent is an alkyl group having from about 7 to about 10 carbon atoms;

up to about 5% propylene glycol;

from about 55 to about 70% ethanol;

water in amount to provide an ethanol:water ratio, by weight, of about 70:30;

base in amount to adjust the pH of the composition in the range of from 6.5 to about 7.5, and, gelling agent in amount effective to thicken the composition.

10. The composition of claim 9 which is free from propylene glycol.

11. A substantially neutral alcoholic or aqueous alcoholic topical composition effective for the transdermal delivery of non-steroidal anti-inflammatory drug which comprises 0.1 to 10% diethylamine salt of diclofenac;

from about 2 to about 15% of $C_7$ to $C_{14}$-hydrocarbyl derivative of 1,3-dioxolane, 1,3-dioxane or acetal as skin penetration enhancer;

up to about 30% propylene glycol;

from about 45 to about 70% of volatile alcohol selected from the group consisting of ethanol, isopropanol and mixtures thereof;

up to about 20% water;

base to provide a pH in the range of from about 6.5 to about 75; and up to about 5% gelling agent.

12. The composition of claim 1 which comprises 2-n-nonyl-1,3-dioxolane as skin penetration enhancing compound.

13. The composition of claim 3 which comprises 2-n-nonyl-1,3-dioxolane as skin penetration enhancing compound.

* * * * *